United States Patent [19]

Masereel et al.

[11] Patent Number: 5,166,162

[45] Date of Patent: Nov. 24, 1992

[54] PYRIDYLSULFONYLUREA AND PYRIDYLSULFONYLTHIOUREA COMPOUNDS

[75] Inventors: Bernard Masereel, Libin; Bernard Pirotte, Oupeye; Marc Schynts, Loncin; Jacques Delarge, Dolambreux, all of Belgium

[73] Assignee: Adir et Compagnie, Courbevoie, France

[21] Appl. No.: 825,142

[22] Filed: Jan. 24, 1992

Related U.S. Application Data

[63] Continuation-in-part of Ser. No. 663,385, Mar. 1, 1991, abandoned.

[30] Foreign Application Priority Data

Mar. 2, 1990 [FR] France ............................. 90 02659
Jan. 6, 1992 [FR] France ............................. 92 00031

[51] Int. Cl.⁵ ................. C07D 213/74; C07D 213/71; A61K 31/44
[52] U.S. Cl. ............................. 514/339; 514/346; 546/272; 546/291
[58] Field of Search ............... 546/272, 291; 514/339, 514/346

[56] References Cited

U.S. PATENT DOCUMENTS

| | | | |
|---|---|---|---|
| Re. 30,633 | 6/1981 | Delarge et al. | 514/332 |
| 4,018,929 | 4/1977 | Delarge et al. | 514/332 |
| 4,042,693 | 8/1977 | Delarge et al. | 514/222.8 |
| 4,055,650 | 10/1977 | Delarge et al. | 514/347 |
| 4,244,950 | 1/1981 | De Ridder et al. | 514/237.2 |
| 4,822,807 | 4/1989 | Topfmeier et al. | 514/347 |
| 4,853,389 | 9/1989 | Dolak et al. | 514/275 |
| 4,954,628 | 9/1990 | Besenyei et al. | 544/211 |

FOREIGN PATENT DOCUMENTS 2267775 11/1975 France .
2416225 8/1979 France .

OTHER PUBLICATIONS

Arzneim. Forsch. 38(I), 1a, 151-152 (1988) Greger.
DeLarge J., Lapiere C. L., De Ridder R., Ghys A. European Journal of Medicinal Chemistry 1981, 16 (1), pp. 65-68.
Pharma Projects, May 1991, p. 31, "Christiaens".

*Primary Examiner*—Mukund J. Shah
*Assistant Examiner*—Matthew V. Grumbling
*Attorney, Agent, or Firm*—Gordon W. Hueschen

[57] ABSTRACT

The invention concerns a compound of formula (I)

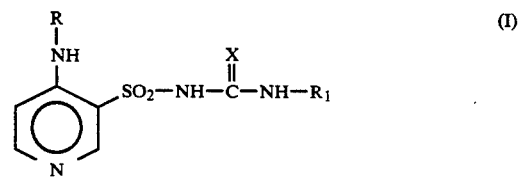

in which:

R represents cycloalkyl, bicycloalkyl or polycycloalkyl,

X represents oxygen or sulfur, and

R1 represents alkyl, cycloalkyl, bicycloalkyl, or polycycloalkyl.

Medicaments thereof and use of same is useful in treating a circulatory ailment related to arterial hypertension or peripheral or cerebral oedema.

19 Claims, No Drawings

PYRIDYLSULFONYLUREA AND PYRIDYLSULFONYLTHIOUREA COMPOUNDS

The present application is a continuation-in-part of our prior-filed copending application Ser. No. 07/663,385, filed Mar. 1, 1991, now abandoned.

The present invention concerns new pyridylsulfonylurea and pyridylsulfonylthiourea compounds, Numerous sulfonylureas and sulfonylthioureas are known in the literature, endowed in particular with diuretic or hypoglycemic properties. Pyridylsulfonylureas like Torasemide, which is a potent diuretic, are also known.

Other pyridylsulfonylureas have also been described on account of their diuretic and anti-inflammatory properties (French Patents No. 2 267 775 and No. 2 416 225).

Their diuretic effect is due to an inhibitory effect of $Na^+/K^+/2Cl^-$ cotransport in the kidneys.

The applicant company has now discovered new pyridylsulfonylureas and pyridylsulphonylthioureas endowed not only with the ability to inhibit $Na^+/K^+/2Cl^-$ cotransport and the passage of chlorides through the kidneys, but also with properties which block the cellular passage of potassium in the kidneys and the lungs.

These new compounds differ from the compounds of the prior art in also having the particularly valuable property of presenting an optimal partition coefficient and optimum pKa for passing through the blood-brain barrier.

The compounds of the invention are thus particularly valuable for the treatment of disorders such as arterial hypertension and edematous conditions of all origins, including cerebral edema.

More specifically the invention concerns compounds of formula (I)

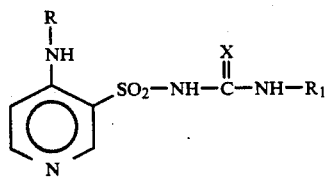

in which:
R represents a cycloalkyl, bicycloalkyl or polycycloalkyl radical having 3 to 15 carbon atoms, optionally interrupted by one or more heteroatoms chosen from among nitrogen, oxygen and sulfur,
X represents an oxygen or sulfur atom,
$R_1$ represents a straight- or branched-chain alkyl radical comprising 1 to 6 carbon atoms or a cycloalkyl, bicycloalkyl or polycycloalkyl radical containing 3 to 15 carbon atoms, optionally interrupted by one or more heteroatoms chosen from among nitrogen, oxygen and sulfur, with the proviso that, when X is an oxygen atom and at the same time R is a monocyclic or bicyclic alkyl radical, $R_1$ cannot represent a linear or branched alkyl radical or a saturated heteromonocyclic group containing nitrogen and able to contain a second heteroatom,
as well as their addition salts with a pharmaceutically acceptable inorganic or organic acid, and, when R or $R_1$ represents a radical having one or more center(s) of asymmetry, their isomers, enantiomers and diastereoisomers.

The invention also encompasses a process for preparing compounds of formula (I), which comprises: either condensing a compound of formula (II)

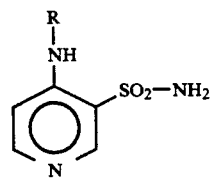

in which R has the same meaning as in formula (I), with an isocyanate or isothiocyanate of formula (III)

in which X and $R_1$ have the same meaning as in formula (I), in the presence of an alkaline agent such as a metal hydroxide or a tertiary amine in a polar solvent, to lead, after neutralization of the reaction medium preceded, if desired, by evaporating the solvent and taking up in water, to compounds of formula (I), which are optionally converted into salts by adding a pharmaceutically acceptable inorganic or organic acid, or which are, if desired, separated into their isomers and then optionally converted into salts by adding a pharmaceutically acceptable inorganic or organic acid,—or condensing a compound of formula (IV)

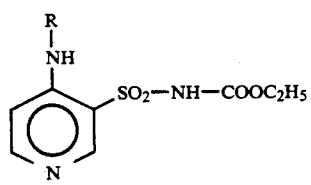

in which R has the same meaning as in formula (I), with an amine of formula (V)

in which $R_1$ has the same meaning as in formula (I), by heating in an anhydrous solvent to obtain, if necessary after purification and neutralization, compounds of formula (I) in which X represents an oxygen atom, which are then be optionally converted into salts by means of a pharmaceutically acceptable inorganic or organic acid, or which are, if desired, separated into their isomers and then optionally converted into salts by adding a pharmaceutically acceptable inorganic or organic acid.

Among pharmaceutically acceptable inorganic or organic acids there may be mentioned, without this list being restrictive, hydrochloric, sulfuric, nitric, acetic, tartaric, malic, maleic, camphoric, methanesulfonic, ethanesulfonic and camphosulfonic acids, and the like.

The compounds of the invention possess very valuable pharmacological properties.

They exhibit diuretic properties due to the inhibition of $Na^+/K^+/2Cl^-$ cotransport and of the passage of chlorides, combined with potassium sparing properties because of inhibition of the membrane passage of potassium.

The compounds of the invention therefore find an application in the treatment of hypertension, being all the more valuable because the normalization of blood pressure is not accompanied by the leakage of potassium, which is known to have harmful effects, particularly for heart muscle.

The compounds of the invention also possess a lipophilic character, particularly well adapted to passing the blood-brain barrier, and consequently their inhibitory effect on Na+/K+/2Cl− cotransport can exert itself directly on the astrocytes, thus preventing the swelling of the astrocytes which represents a very important part of cerebral edema.

The compounds of the invention therefore find an application in the treatment of edematous conditions and particularly cerebral edema.

Pharmaceutical compositions containing as active principle at least one compound of formula (I) or one of its addition salts with a pharmaceutically acceptable acid, alone or in combination with one or more inert nontoxic excipients or vehicles, are also the subject of the present invention.

Among pharmaceutical compositions according to the invention there may be mentioned more particularly those which are suitable for oral, parenteral, nasal, rectal or cutaneous administration, particularly simple or sugared tablets, capsules, pills and sachets, sublingual tablets, suppositories, skin creams and gels, aerosols, injectable solutions, nasal drops, and the like.

The effective dosage varies according to the age and weight of the patient, the severity of the affection, and also the route of administration. In general, unit dosages range between 0.1 and 500 mg in 1-3 doses daily.

The following examples illustrate the invention, without limiting it in any way.

Starting compounds of general formulae (II) and (IV) are described in the literature (Eur. J. Med. Chem. 15 (4), 299–304 (1980) and 16 (1), 65–68 (1981)) or can be prepared in a similar way.

Compounds of formula (II) can be obtained, in particular, by the action of an excess of an amine of formula RNH$_2$, where R has the same meaning as in general formula (I), on a pyridine derivative of formula

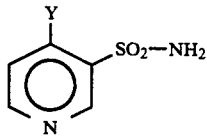

in which Y represents a starting group such as a halogen or SO$_3$H, by heating between 80° and 140° C. If necessary after dilution and making the mixture alkaline and then, if desired, clarifying with charcoal, the compounds of formula (II) are precipitated at pH 7-8, spun down, dried and utilized as such in the following reactions.

In the examples that follow, the percentage analysis, and infra-red and $^1$H NMR spectra agree with those of the expected structures.

EXAMPLE 1

N-((4-(-cyclohexylamino)pyrid-3-yl)sulfonyl)-N'-cyclohexylurea 0.01 mol of NaOH dissolved in a minimum of water is added to a solution of 0.01 mol of (4-(cyclohexylamino)-pyrid-3-yl)sulfonamide in 80 ml of a water/acetone mixture (1:1). The mixture is stirred with a magnetic rod, and 0.015 mol of cyclohexylisocyanate is added. Stirring is continued, while the reaction is followed by TLC (silica gel 60F254, mobile phase: ethyl acetate 9, methanol 1, triethylamine 0.2). Gentle heating can accelerate the reaction. The mixture is evaporated under reduced pressure, and the residue is taken up in 100 ml of 0.2N NaOH. Any insoluble material is filtered out and the solution is corrected to pH 6.5-7 and left to crystallize for 1 hour in the refrigerator. The precipitate collected is suspended in 100 ml of a water/acetone mixture (4:1) saturated with NaHCO$_3$. The mixture is stirred for 1 hour and then filtered, and the filtrate is brought back to pH 6.5-7 and left to crystallize in the refrigerator. The crystals are collected, washed in cold water and dried under vacuum at normal temperature. Yield is around 50-60%. Melting point: 165°–167° C.

EXAMPLE 2

N-((4-(cycloheptylamino)pyrid-3-yl)sulfonyl)-N'-cyclohexylurea 40 ml of anhydrous toluene are added to 0.01 mol of ethyl N-(4-cycloheptylamino)pyrid-3-yl)sulfonyl carbamate, 0.05 mol of cyclohexylamine and 3 g of 4 Å molecular sieve, and subjected to reflux for several hours, with the reaction being followed by TLC (silica gel 60F254; mobile phase: ethyl acetate 9, methanol 1, acetic acid 0.2). The molecular sieve is separated out and the mixture is evaporated under reduced pressure. The residue is taken up in 100-150 ml of 0.2N NaOH, and extracted twice with 50 ml of ether. The aqueous phase is corrected to pH 6.5-7 and left to crystallize for 1 hour in the refrigerator. The procedure is then continued as in Example 1. Yield is around 50-60%. Melting point: 165°–169° C.

EXAMPLE 3

N-((4-(cyclooctylamino)pyrid-3-yl)sulfonyl-N'-cyclooctylurea nitrate

The same operating conditions are used as in Example 2, but with ethyl N-(4-(cyclooctylamino)pyrid-3-yl)sulfonyl carbamate and cyclooctylamine being used as the starting materials. After separating out the molecular sieve and evaporating under reduced pressure, the mixture is taken up in 75-100 ml of 0.2N NaOH and extracted twice with 50 ml of ether, and 5-10 ml of nitric acid is added to the aqueous phase. It is then left overnight in the refrigerator.

The crystals are collected on filter paper, washed with a minimum of iced water and dried under vacuum at normal temperature. Yield is around 60-70%. Melting point: 144°–146° C.

EXAMPLE 4

N-((4-(cycloheptylamino)pyrid-3-yl)sulfonyl)-N'-cyclohexylthiourea 0.01 mol of NaOH dissolved in a minimum of water is added to a solution of 0.01 mol of (4-(cycloheptylamino)pyrid-3-yl)sulfonamide in 80 ml of a water/acetone mixture (1:1). The mixture is stirred with a magnetic rod, and 0.015 mol of cyclohexylisothiocyanate is added. Stirring is continued, while the reaction is followed by TLC (silica gel 60F254; mobile phase: ethyl acetate 9, methanol 1, triethylamine 0.2). Gentle heating can accelerate the reaction. The mixture is evaporated under reduced pressure and the residue is taken up in 100 ml of 0.2N NaOH. Any insoluble material is filtered out and the solution is corrected to pH 6.5–7 and left to crystallize for 1 hour in the refrigerator. The precipitate collected is suspended in 100 ml of a water/acetone mixture (4:1) saturated with NaHCO₃. The mixture is stirred for 1 hour and then filtered, and the filtrate, brought back to pH 6.5–7, is left to crystallize in the refrigerator. The crystals are collected, washed in cold water and dried under vacuum at normal temperature. Yield is around 50–60%. Melting point: 195°–197° C.

EXAMPLE 5

N-((4-((bicyclo[2.2.1]hept-1-yl)amino)pyrid-3-yl)sulfonyl)-N'-(4-((bicyclo[2.2.1]hept-1-yl)amino)pyrid- 2 g of (4-(bicyclo[2.2.5]heptanylamino)pyrid-3-yl)sulfonamide are dissolved in 20 ml of acetone and 5 ml of isopropylisothiocyanate and 5 ml triethylamine are added. The mixture is heated under reflux while the reaction is followed by TLC (silica gel 60F254; mobile phase: ethyl acetate 9, methanol 1, triethylamine 0.2). It is evaporated to dryness, taken up in 120 ml of 0.2N NaOH and filtered. The solution is extracted 3 times with 150 ml of ether, clarified with charcoal and corrected to pH 7.5. The product crystallizes out. Yield is around 50%. Melting point: 194°–196° C.

EXAMPLE 6

N-((4-(cyclooctylamino)pyrid-3-yl)sulfonyl)-N'-ethylthiourea

The procedure is identical to that of Example 5, using (4-(cyclooctylamino)pyrid-3-yl)sulfonamide and ethylisothiocyanate as the starting materials. Yield is similar. Melting point: 196°–198° C.

By using the procedures described in the preceding examples, the compounds of Examples 7 to 17 are obtained in the same way.

EXAMPLE 7

N-((4-(cyclohexylamino)pyrid-3-yl)sulfonyl)-N'-cyclooctylurea

Melting point: 133°–137° C.

EXAMPLE 8

N-((4-(cyclooctylamino)pyrid-3-yl)sulfonyl)-N'-cycloheptylurea

Melting point: 156°–160° C.

EXAMPLE 9

N-((4-(cyclohexylamino)pyrid-3-yl)sulfonyl)-N'-cycloheptylurea

Melting point: 145°–150° C.

EXAMPLE 10

N-((4-(cyclooctylamino)pyrid-3-yl)sulfonyl)-N'-cyclohexylurea

Melting point: 144°–148° C.

EXAMPLE 11

N-((4-(cycloheptylamino)pyrid-3-yl)sulfonyl)-N'-cyclooctylurea

Melting point: 140°–145° C.

EXAMPLE 12

N-((4-(cyclododecylamino)pyrid-3-yl)sulfonyl)-N'-ethylurea

Melting point: 195°–196° C.

EXAMPLE 13

N-((4-(cyclododecylamino)pyrid-3-yl)sulfonyl)-N'-isopropylurea

Melting point: 126°–128° C.

EXAMPLE 14

N-((4-(cycloheptylamino)pyrid-3-yl)sulfonyl)-N'-isopropylthiourea

Melting point: 196°–198° C.

EXAMPLE 15

N-((4-(cyclooctylamino)pyrid-3-yl)sulfonyl)-N'-isopropylthiourea

Melting point: 194°–195° C.

EXAMPLE 16

N-((4-(cyclohexylamino)pyrid-3-yl)sulfonyl)-N'-ethylthiourea

Melting point: 186°–187° C.

EXAMPLE 17

N-((4-(2-(aza-2-bicyclo[3.3.0]octyl)amino)pyrid-3-yl)sulfonyl-N'-isopropylurea

Melting point: 185°–186° C.

EXAMPLE 18

N-((4-(cycloheptylamino)pyrid-3-yl)sulfonyl)-N'-cycloheptylurea

Melting point: 172°–174° C.

Microanalysis: Calculated C: 58.80, H: 7.89, N: 13.71, S: 7.85. Found C: 58.75, H: 7.83, N: 13.92, S: 7.66.

EXAMPLE 19

Determination of partition coefficients and pKa

The coefficients of partition between n-octanol and water were determined at pH=7.4 by conventional techniques and are expressed as logarithms to base 10 (Log P).

The pKa values represent the proton acidity constants of $SO_2$—NH—CO—.

| EXAMPLES | Log P | pKa |
| --- | --- | --- |
| Torasemide | 0.449 | 6.82 |
| Ex 1 | 1.331 | 9.02 |
| Ex 2 | 1.665 | 9.39 |
| Ex 3 | 2.704 | 7.74 |
| Ex 7 | 2.074 | 9.13 |
| Ex 8 | 2.449 | 9.15 |
| Ex 10 | 2.063 | 8.95 |

These results indicate a lipophilic character at physiological pH which would favor passage through the blood-brain barrier.

EXAMPLE 20

Inhibition of Na+/K+/2Cl− cotransport and Cl− passage

The 50% inhibitory concentration for Na+/K+/2Cl− cotransport in vivo is decreased, in the case of the compound of Example 3, by about 60% relative to Torasemide (luminal membrane of the ascending branch of the loop of Henlé in the nephron of perfused rabbits (Arzneim. Forsch. (1988) 38 (1a), 151–152)), and by 85% relative to Torasemide in the case of the compound of Example 10 (erythrocyte membrane in normotensive rats).

This decrease of the 50% inhibitory concentration of the Torasemide for Na+/K+/2Cl+ co-transport (erythrocyte membrane in normotensive rats) reachs even 90% in the case of the compound of Example 18.

The 50% inhibitory concentration for Cl− passage in the kidneys in vivo is decreased, in the case of the compound of Example 8 by about 50% relative to Torasemide and in the case of the compound of Example 18 by 75%.

EXAMPLE 21

Tablets containing 5 mg of N-((4-(cyclohexylamino)pyrid-3-yl)sulfonyl)-N′-cyclohexylurea

| Formulation for 10,000 tablets | |
| --- | --- |
| N-((4-(cyclohexylamino)pyrid-3-yl)sulfonyl)-N′-cyclohexylurea | 50 grams |
| Lactose | 150 grams |
| Corn starch | 750 grams |
| Colloidal silica | 2 grams |
| Magnesium stearate | 1 gram |

We claim:

1. A compound selected from those of formula (I)

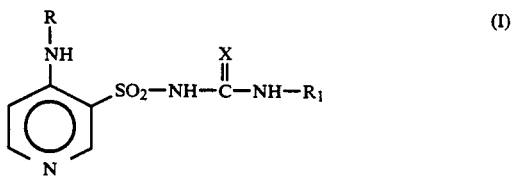

in which:

R represents monocycloakyl bicycloalkyl, or polycycloalkyl having 3 to 15 carbon atoms, optionally having in its skeleton one or more heteroatoms chosen from nitrogen, oxygen and sulfur, X represents oxygen or sulfur, $R_1$ represents straight- or branched-chain alkyl having 1 to 6 carbon atoms or monocycloakyl, bicycloalkyl, or polycycloalkyl having 3 to 15 carbon atoms, optionally containing on its skeleton one or more heteroatoms chosen from nitrogen, oxygen and sulfur, with the proviso that, when X is an oxygen atom and at the same time R is monocyclic or bicyclic alkyl or heteromonocycloalkyl, $R_1$ cannot represent linear or branched alkyl or heteromonocycloalkyl, as well as its addition salts with a pharmaceutically-acceptable inorganic or organic acid, and, when R or $R_1$ represents a radical comprising one or more centers of asymmetry, its isomers, enantiomers and diastereoisomers.

2. A compound as claimed in claim 1, wherein R and $R_1$ represent cycloalkyl, bicycloalkyl, or polycycloalkyl having 3 to 15 carbon atoms, optionally interrupted by one or more nitrogen atoms, or an enantiomer or a diastereoisomer thereof.

3. Compound of claim 1 being N-(4-(cyclohexylamino)pyrid-3-yl)sulfonyl)-N′-cyclohexylurea or a salt thereof.

4. Compound of claim 1 being N-((4-(cycloheptylamino)pyrid-3-yl)sulfonyl)-N′-cyclohexylurea or a salt thereof.

5. Compound of claim 1 being N-((4-(cyclooctylamino)pyrid-3-yl)sulfonyl)-N′-cyclooctylurea or a salt thereof.

6. Compound of claim 1 being N-((4-(cycloheptylamino)pyrid-3-yl)sulfonyl)-N′-cyclohexylthiourea or a salt thereof.

7. Compound of claim 1 being N-((4-bicyclo[2.2.1-]hept-1-ylamino)pyrid-3-yl)sulfonyl)-N′-isopropylthiourea or a salt thereof.

8. Compound of claim 1 being N-((4-(cyclooctylamino)pyrid-3-yl)sulfonyl)-N′-ethylthiourea or a salt thereof.

9. Compound of claim 1 being N-((4-(cyclododecylamino)pyrid-3-yl)sulfonyl)-N′-ethylurea or a salt thereof.

10. Compound of claim 1 being N-((4-(2-(aza-2-bicyclo[3.3.0]octyl)amino)pyrid-3-yl)sulfonyl)-N′-isopropylurea, a salt or a diastereoisomer thereof.

11. Compound of claim 1 being N-((4-(cycloheptylamino)pyrid-3-yl)sulfonyl)-N′-cycloheptylurea or a salt thereof.

12. A pharmaceutical composition containing as active principle a compound as claimed in claim 1 in combination with a pharmaceutically-acceptable carrier or diluent.

13. A pharmaceutical composition containing as active principle a compound as claimed in claim 11 in combination with a pharmaceutically-acceptable carrier or diluent.

14. A method for treating a living animal body afflicted with a circulatory ailment related to arterial hypertension or oedema comprising the step of administering to the said living animal an amount of a compound of claim 1 which is effective for the alleviation of the said ailment.

15. A method for treating a living animal body afflicted with a circulatory ailment related to arterial hypertension or peripheral or cerebral oedema comprising the step of administering to the said living animal an amount of a compound of claim 11 which is effective for alleviation of the said ailment.

16. Method of claim 14 wherein the ailment is cerebral oedema.

17. Method of claim 15 wherein the ailment is cerebral oedema.

18. Compound of claim 1 which is N-((4-(cyclooctylamino)pyrid-3-yl)sulfonyl)-N′-cycloheptylurea or a salt thereof.

19. Compound of claim 1 which is N-((4-(cyclooctylamino)pyrid-3-yl)sulfonyl)-N′-cyclohexylurea or a salt thereof.

* * * * *

UNITED STATES PATENT AND TRADEMARK OFFICE
CERTIFICATE OF CORRECTION

PATENT NO. : 5,166,162

DATED : Nov. 24, 1992

INVENTOR(S) : Bernard Masereel, Bernard Pirotte, Marc Schynts, Jacques Delarge It is certified that error appears in the above-identified patent and that said Letters Patent is hereby corrected as shown below:

Column 5, line 15; "fonyl )-N'(4-((bicyclo[2.2.1]hept-1-yl)amino)pyrid" should read -- fonyl)-N'-isopropylthiourea --.

Column 5, line 16; "2 g of (4-bicyclo[2.2.5]heptanylamino)pyrid-3-yl)sul-" should read --2 g of (4-((bicyclo[2.2.1[hept-1-yl)amino)pyrid-3-yl)sul- --.

Column 7, line 58; "containing on its" should read -- containing in its --

Column 8, line 21; move the closing bracket "]" from the beginning of line 21 to the end of line 20 and insert after "1".

Column 8, approximately line 52; delete "peripheral or cerebral".

Signed and Sealed this

Twenty-third Day of November, 1993

*Attest:*

BRUCE LEHMAN

*Attesting Officer*  *Commissioner of Patents and Trademarks*